(12) United States Patent
Wenzel et al.

(10) Patent No.: US 6,562,921 B1
(45) Date of Patent: May 13, 2003

(54) CATALYST PRECURSOR COMPOUND AND OLEFIN POLYMERIZATION PROCESS USING SAME

(75) Inventors: Timothy T. Wenzel, Charleston, WV (US); Robert D. Froese, Charleston, WV (US); Thomas Henry Peterson, Charleston, WV (US)

(73) Assignee: Univation Technologies, LLC, Houston, TX (US)

( * ) Notice: Subject to any disclaimer, the term of this patent is extended or adjusted under 35 U.S.C. 154(b) by 0 days.

(21) Appl. No.: 09/976,980

(22) Filed: Oct. 12, 2001

(51) Int. Cl.⁷ .................................................. C08F 4/52
(52) U.S. Cl. ........................ 526/160; 526/170; 526/169; 526/169.2; 526/348; 526/348.3; 526/348.5; 526/348.2; 526/348.6; 526/351; 526/352; 502/103; 502/117
(58) Field of Search .................................. 526/170, 160

(56) References Cited

U.S. PATENT DOCUMENTS 5,646,322 A * 7/1997 van Beek et al. ............. 556/11

OTHER PUBLICATIONS

Erker, G.; Wilker, S.; Kruger, C.; Goddard, R. J. Am. Chem. Soc. 1992, 114, 10983–10984.*

Rieger, B. J. Organomt.Chem. 1992, 428, C33–C36.*

Steinhorst, A.; Erker, G.; Grehl, M.; Frohlich, R. J. Organomet. Chem. 1997, 542, 191–204.*

Eğe, S. "Organic Chemistry: Structure and Reactivity" 3$^{rd}$ Ed. 1994, D.C. Heath and Company: Lexington, MA, p. 219–226.*

* cited by examiner

Primary Examiner—David W. Wu
Assistant Examiner—Rip A. Lee
(74) Attorney, Agent, or Firm—Lisa Kimes Jones; Kevin M. Faulkner

(57) ABSTRACT

A catalyst precursor compound useful for the polymerization of olefins. The compound comprises a metal atom and two π-bonded aromatic ring systems which are bridged by being linked to adjacent members of a ring structure in cis fashion.

28 Claims, No Drawings

CATALYST PRECURSOR COMPOUND AND OLEFIN POLYMERIZATION PROCESS USING SAME

FIELD OF THE INVENTION

The present invention relates to catalyst precursor compounds which in combination with an activator forms a catalyst composition that is useful for the polymerization of olefin(s). The catalyst precursor compound comprises a metal atom and two π-bonded aromatic ring systems, where the aromatic ring systems are linked together by a bridging group comprising a ring, such that the aromatic ring systems are linked to adjacent members of the ring, either directly or through another group, in cis fashion. The present invention also relates to a method of preparing such catalyst precursor compounds, catalyst compositions comprising these catalyst precursor compounds, and polymerization processes utilizing same.

BACKGROUND OF THE INVENTION

A variety of catalyst compositions containing single site catalyst precursors have been shown to be highly useful in the preparation of polyolefins, producing relatively homogeneous copolymers at good polymerization rates. In contrast to traditional Ziegler-Natta catalyst compositions, single site catalyst compositions such as metallocene catalysts comprise catalytic compounds in which each catalyst composition molecule contains one or only a few polymerization sites, thereby allowing one to tailor the properties of the finished polymer.

There is a continuous need in the art to provide new and varied single site catalysts that can produce new and/or tailored polyolefins. There are several possible ways of modifiying the structure of already known single site catalyst precursor compounds to arrive at new catalysts and, thus new polymer products. One of these possible modifications involves the moiety which bridges two cyclopentadienyl or related ligands of a metallocene catalyst precursor compound. Compounds having cyclic bridging moieties are described in the literature. However, the stereochemistry of the bonds between the cyclopentadienyl ligands and the cyclic bridging group in the catalyst precursor compound and its utilization for influencing the properties of the corresponding catalyst system and the polymer made thereby have not received much attention so far.

B. Rieger, J. Organometallic Chem. 1992, 428, C33–36, fully incorporated herein by reference, describes the preparation of trans-1,2-cyclohexylenebis (1-indenyl)zirconium dichloride and the use thereof as catalyst for the polymerization of propylene. Furthermore, A. Steinhorst et al, J. Organometallic Chem. 1997, 542, 191–204, fully incorporated herein by reference, report on the preparation and use as catalyst precursors for the polymerization of propylene, respectively, of a series of trans-1,2-cycloalkylene-bridged bis(indenyl or tetrahydroindenyl)MCl$_2$ species (M=Ti, Zr, Hf) wherein the cycloalkylene bridge has 5 to 8 members.

According to the present invention, the combination of activator (cocatalyst) and single site catalyst precursor compounds comprising two aromatic ring systems π-bonded to a metal atom and linked in cis fashion to adjacent (vicinal) ring members of a cyclic bridging group are very effective for the polymerization of olefins. Moreover, it has been found that this particular way of bridging the aromatic ring systems can be used to constrain the geometry around the metal atom, thereby influencing the structure of the polymer chains obtainable from the corresponding catalyst composition.

SUMMARY OF THE INVENTION

The present invention provides a catalyst precursor compound including a metal selected from Groups 3 to 12 and the lanthanide and actinide series of the Periodic Table of Elements and two π-bonded aromatic ring systems. The aromatic ring systems are linked by a bridging group which comprises a 3 to 12-membered ring, where the aromatic ring systems are linked to adjacent members of the ring, either directly or through another group, in cis fashion. The invention also provides methods for preparing the catalyst precursor compound, catalyst compositions incorporating the catalyst precursor compound and polymerization processes utilizing same.

DETAILED DESCRIPTION

A new catalyst precursor compound has been discovered which includes a metal selected from Groups 3 to 12 and the lanthanide and actinide series of the Periodic Table of Elements and two π-bonded aromatic ring systems. The aromatic ring systems are linked by a bridging group which comprises a 3- to 12-membered ring, where the aromatic ring systems are linked to adjacent members of the bridging ring, either directly or through another group, in cis fashion.

The metal atom is selected from Groups 3 through 12 and the lanthanide or actinide series of the Periodic Table of Elements. Preferably the metal atom is selected from Groups 3 to 10 and the lanthanide series, more preferably from Groups 4, 5 and 6, more preferably from Group 4 and most preferably the metal atom is Zr or Hf.

The aromatic ring systems of the catalyst precursor compound are bonded to the metal atom. The aromatic ring systems (which can be the same or different) are typically composed of atoms selected from Groups 13 to 16 of the Periodic Table of Elements. Preferably the atoms are selected from carbon, nitrogen, oxygen, silicon, sulfur, phosphorus, germanium, boron, aluminum and combinations thereof. Most preferably, the aromatic rings or ring systems are composed of or comprised carbon atoms such as, but not limited to, unsubstituted or substituted, cyclopentadienyl and cyclopentadienyl-type ligands ("cyclopentadienyl-type" meaning a ligand comprising a cyclopentadienyl or related structure, e.g., a structure wherein one or more carbon atoms of a cyclopentadienyl ligand are replaced by one or more heteroatoms such as, e.g., N, O and S). Non-limiting examples thereof include unsubstituted and substituted cyclopentadienyl, indenyl, benzindenyl, fluorenyl, azulenyl, pyrrolyl, pyrazolyl, carbazolyl and borabenzene ligands and the like, including hydrogenated versions thereof, for example, tetrahydroindenyl, tetrahydrofluorenyl and octahydrofluorenyl ligands.

Independently, each of the two aromatic rings or ring systems may optionally be substituted with one or more substituent groups. Non-limiting examples of substituent groups are linear, branched and cyclic alkyl, alkenyl and alkynyl radicals, aryl, arylalkyl and alkylaryl radicals, acyl radicals, aroyl radicals, alkoxy radicals, aryloxy radicals, alkylthio radicals, dialkylamino radicals, alkoxycarbonyl radicals, aryloxycarbonyl radicals, carbamoyl radicals, alkyl- and dialkylcarbamoyl radicals, acyloxy radicals, acylamino radicals, aroylamino radicals and combinations thereof. In a preferred embodiment the substituent groups, if any, have up to 50 non-hydrogen atoms, e.g., from 1 to 30 carbon atoms, more preferably from 1 to 20 carbon atoms, most preferably from 1 to 12 carbon atoms. Moreover these substituent groups may also be halogenated, e.g., fluorinated and/or chlorinated. Illustrative, non-limiting examples of substituents include methyl, ethyl, propyl, butyl, pentyl, hexyl, cyclopentyl, cyclohexyl, benzyl, phenyl, tolyl and xylyl groups and the like, including all their isomers, for example tertiary butyl, isopropyl, and the like. Further non-limiting examples of other possible substituents include hydrocarbyl substituted organometalloid radicals such as, e.g., trimethylsilyl, trimethylgermyl, methyldiethylsilyl and the like; halocarbyl-substituted organometalloid radicals including tris(trifluoromethyl)silyl, methyl-bis (difluoromethyl)silyl, bromomethyl-dimethylgermyl and the like; and disubstituted boryl radicals including dimethylboryl and the like; disubstituted pnictogen radicals including dimethylamino, dimethylphosphino, diphenylamino, methylphenylphosphino and the like; and chalcogen radicals including methoxy, ethoxy, propoxy, phenoxy, methylthio, ethylthio and the like. In general, the non-hydrogen atoms of the substituents are selected from carbon, silicon, boron, aluminum, nitrogen, phosphorus, oxygen, tin, sulfur, germanium and the halogens. Also, at least two substituent groups, preferably two adjacent substituent groups, may be joined to form a ring structure having from 3 to 30 members selected from carbon, nitrogen, oxygen, phosphorous, silicon, germanium, aluminum, boron and combinations thereof.

Preferred aromatic ring systems for the purposes of the present invention are cyclopentadienyl, indenyl, fluorenyl and benzindenyl ligands as well as partially hydrogenated forms thereof, in particular 1-indenyl. Also, these ring systems are preferably unsubstituted or substituted with not more than 4 substituents having from 1 to 4 carbon atoms. A particularly preferred substituent is methyl.

The bridging group linking the aromatic ring systems comprises a 3 to 12 membered ring, preferably a 5 to 12 membered ring, more preferably a 5 to 8 membered ring, more preferably a ring having greater than 4 ring members, and most preferably a ring having 5 or more ring members. This ring may be saturated or partially unsaturated, unsubstituted or substituted, and may also be part of a fused, polycyclic ring system or any other moiety that comprises more than one ring. The ring members are usually selected from carbon, nitrogen, oxygen, silicon, sulfur, phosphorus, germanium, boron, aluminum and combinations thereof, with B, C, Si, N, P, O and S being preferred and C, Si, N and O being most preferred. The ring preferably comprises at least 4, at least 5, or less than 8 ring members.

Still referring to the ring of the bridging group, preferably not more than 3, more preferably not more than 2, and most preferably not more than 1 ring member is different from carbon. Examples of heteroatom containing bridging group rings include morpholine, thiomorpholine, dioxane, piperazine, piperidine, tetrahydropyran, tetrahydro-furan, tetrahydrothiophene, pyrazoline, pyrazolidine, pyrroline, pyrrolidine and the like. Particularly preferred are carbocyclic rings such as, e.g., cycloaliphatic rings (e.g., cyclopentane, cyclopentene, cyclohexane, cyclohexene, cycloheptane, cycloheptene, tetrahydronaphthalene, decahydronaphthalene, tetrahydrofluorene and octahydrofluorene rings).

Furthermore, the ring may optionally be substituted with one or more substituent groups. Non-limiting examples of substituent groups are halogen (e.g., F, Cl, Br), hydroxy, linear, branched and cyclic alkyl, alkenyl and alkynyl radicals, aryl, arylalkyl and alkylaryl radicals, acyl radicals, aroyl radicals, alkoxy radicals, aryloxy radicals, alkylthio radicals, dialkylamino radicals, alkoxycarbonyl radicals, aryloxycarbonyl radicals, carbamoyl radicals, alkyl- and dialkylcarbamoyl radicals, acyloxy radicals, acylamino radicals, aroylamino radicals and combinations thereof. In a preferred embodiment the substituent groups, if any, have up to 50 non-hydrogen atoms, from 1 to 30 carbon atoms, preferably from 1 to 20 carbon atoms, for example, from 1 to 12 carbon atoms. Moreover, the carbon containing substituent groups may be halogenated, e.g., fluorinated and/or chlorinated. Non-limiting examples of suitable substituents include methyl, ethyl, propyl, butyl, pentyl, hexyl, cyclopentyl, cyclohexyl, benzyl, phenyl, tolyl and xylyl groups and the like, including all their isomers, for example tertiary butyl, isopropyl, and the like. Further non-limiting examples of suitable substituents include hydrocarbyl substituted organometalloid radicals such as, e.g., trimethylsilyl, trimethylgermyl, methyldiethylsilyl and the like; halocarbyl-substituted organometalloid radicals including tris(trifluoro-methyl)silyl, methyl-bis(difluoromethyl) silyl, bromomethyl-dimethylgermyl and the like; and disubstituted boryl radicals including dimethylboryl, and the like; disubstituted pnictogen radicals including dimethylamino, dimethylphosphino, diphenylamino, methylphenylphosphino, and the like; and chalcogen radicals including methoxy, ethoxy, propoxy, phenoxy, methylthio, ethylthio, and the like. In general, the non-hydrogen atoms of the substituents are selected from carbon, silicon, boron, aluminum, nitrogen, phosphorus, oxygen, tin, sulfur, germanium and the halogens. Also, at least two substituent groups, preferably two adjacent substituent groups, may be joined to form a ring structure having from 3 to 30 members selected from carbon, nitrogen, oxygen, phosphorus, silicon, germanium, aluminum, boron and combinations thereof. Preferably, the ring is either unsubstituted or substituted by not more than 4, more preferred not more than 3, and most preferred not more than 2 substituents. Even if only one substituent is present, it preferably does not comprise more than 4, more preferred not more than 3, e.g., 1 or 2, non-hydrogen atoms. A non-limiting example of a preferred substituent is methyl.

If one or more substituents are present on the ring, they are usually linked to ring members different from those which the aromatic ring systems are linked to.

Preferably not more than one of the ring members is different from a carbon atom. Preferably the bridging group contains a cycloaliphatic ring, for example, a ring having 5 to 8 members, preferably 6 to 8 members, and more preferably contains a cis-1,2-cyclohexylene group.

In a preferred embodiment, the aromatic ring systems are linked to adjacent ring members that are capable of bonding them in cis fashion. More preferably, the adjacent ring members are carbon atoms.

Additional ligands may be bonded to the Group 3 to 12 metal, such as at least one leaving group. In one embodiment, the leaving group is a monoanionic labile ligand having a sigma-bond to the metal. The number of additional ligands depends on the oxidation state of the metal and is such a that a neutral species is formed. For example, in the case of a Group 4 metal such as Zr two additional ligands are usually bonded to the metal. These additional ligands may be the same or different.

Non-limiting examples of additional ligands include weak bases such as amines, phosphines, ethers, carboxylates, dienes, hydrocarbyl radicals having from 1 to 20 carbon atoms, hydrides, halogens and combinations thereof. Also, two or more additional ligands may form a part of a fused ring or ring system. Other non-limiting examples of additional ligands include the above-described substituent groups for the aromatic ring systems and the ring structure they are linked to, including cyclobutyl, cyclohexyl, heptyl, tolyl, trifluoromethyl, tetramethylene, pentamethylene, methylidene, methyoxy, ethyoxy, propoxy, phenoxy, bis(N-methylanilide), dimethylamide, dimethylphosphide radicals and the like.

Preferred additional ligands are selected from hydrogen, halogen, hydroxy, amino, alkyl, alkoxy, aryl, aryloxy, alkenyl, arylalkyl, alkylaryl and arylalkenyl groups; or two additional ligands are joined together to form an alkanediyl group or a conjugated diene ligand which is coordinated to the metal in a metallacyclopentene fashion; or two additional ligands represent a conjugated diene which forms a π-complex with the metal atom. Particularly preferred additional ligands are chlorine, $C_1$–$C_6$ alkyl groups, $C_6$–$C_{10}$ aryl groups, $C_7$–$C_{12}$ arylalkyl groups and $C_7$–$C_{12}$ alkylaryl groups.

In another embodiment, the catalyst precursor compound of the invention is represented by Formula I.

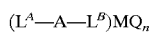

$(L^A\text{—}A\text{—}L^B)MQ_n$     Formula I wherein M is a metal selected from Groups 3 to 10 and the lanthanide series of the Periodic Table of Elements, and $L^A$ and $L^B$ bonded to M are independently selected from cyclopentadienyl ligands and cyclopentadienyl-type ligands. A is a linking group containing a 4 to 8 membered ring. $L^A$ and $L^B$ are bonding to adjacent members of A in cis fashion. Each Q is bonded to M and is independently a monoanionic ligand, or two radicals Q together form a divalent anionic chelating ligand. Depending on the formal oxidation state of M, n is 0, 1 or 2.

In another embodiment, in Formula I, M is selected from Groups 3 to 10, more preferably from Groups 4 to 6, and more preferably from Group 4. In another embodiment M is Zr or Hf, preferably Zr.

In another embodiment, in Formula I, $L^A$ and $L^B$ are independently selected from substituted or unsubstituted cyclopentadienyl, indenyl and fluorenyl groups and preferably at least one of $L^A$ and $L^B$ represents a cyclopentadienyl or indenyl group.

In another embodiment, in Formula I, A comprises a 4 to 8 membered ring, preferably not more than one ring member is different from a carbon atom. A may comprise a cycloaliphatic ring such as, e.g., a cyclopentane or cyclohexane ring. Preferably A is or includes a 1,2 cyclohexylene group.

In another embodiment, in Formula I, each Q is independently selected from hydrogen, halogen, hydroxy, amino, alkyl, alkoxy, aryl, aryloxy, alkenyl, arylalkyl, alkylaryl and arylalkenyl groups. Additionally, two radicals Q may be joined together to form an alkanediyl group or a conjugated diene ligand which is coordinated to M in a metallacyclopentene fashion or may represent a conjugated diene which forms a π-complex with M. Preferably, the radicals Q are independently selected from halogen, $C_1$–$C_6$ alkyl groups, $C_6$–$C_{10}$ aryl groups, $C_7$–$C_{12}$ arylalkyl groups and $C_7$–$C_{12}$ alkylaryl groups.

In a preferred embodiment, in Formula I, M is a Group 4 atom, preferably zirconium or hafnium, $L^A$ and $L^B$ are independently selected from cyclopentadienyl, 1-indenyl and 9-fluorenyl groups, A represents a 6 to 8 membered cycloaliphatic group. Each Q is halogen, preferably chlorine, a $C_1$–$C_6$ alkyl groups, a $C_6$–$C_{10}$ aryl groups, a $C_7$–$C_{12}$ arylalkyl groups or a $C_7$–$C_{12}$ alkylaryl group. In another preferred embodiment, M is zirconium, $L^A$ and $L^B$ are 1-indenyl groups, A is an unsubstituted cis-1,2-cyclohexylene group and each Q is chlorine or methyl.

In another embodiment, cis compounds represented by the above formula $L^A$—A—$L^B$ are prepared by reacting a compound represented by the formula $L^A$—A—O—$SO_2R_F$, wherein $R_F$ is a fluorinated hydrocarbyl (preferably fluorinated alkyl) group and $L^A$ and O—$SO_2R_F$ are bonded to adjacent members of the ring of A in trans fashion with a compound of formula $E^+ L^{B-}$ where $E^+$ represents a cation. For example, $R_F$ may be a fluorinated methyl or ethyl group, and preferably it is trifluoromethyl. $E^+ L^{B-}$ may, for example, represent an alkali metal (e.g., Li, Na, or K) salt of cyclopentadiene or a compound comprising a cyclopentadiene structure such as, e.g. indene, tetrahydroindene and fluorene.

In another embodiment, the trans intermediate of formula $L^A$—A—O—$SO_2R_F$ can be obtained, for example, by reacting a precursor compound of A which contains an epoxidized ring (e.g., an epoxidized cycloalkene such as cyclohexene oxide or cyclopentene oxide) with a compound of formula $D^+ L^{A-}$ where $D^+$ represents a cation and hydrolyzing the resultant intermediate to form a compound of formula $L^A$—A—OH where $L^A$ and OH are bonded to adjacent members of the ring of A in trans fashion. The OH group of the latter compound is converted into a group of formula O—$SO_2R_F$, for example, by reaction with a trifluoromethanesulfonate species (such as, e.g., trifluoromethanesulfonic anhydride). $D^+ L^{A-}$ may, for example, represent an alkali metal (e.g., the Li, Na, or K) salt of cyclopentadiene or a compound comprising a cyclopentadiene structure such as, e.g. indene, tetrahydroindene and fluorene. It may be the same as or different from $E^+ L^{B-}$, mainly depending on whether $L^A$ and $L^B$ are to be the same or different.

The catalyst precursor compound of the present invention may be synthesized by any means, and the invention is not limited thereby. For example, preferred methods of making the catalyst precursor compound, including the individual stereoisomers thereof, are illustrated in Examples 4 to 6 below.

In another embodiment, the catalyst precursor compound of the invention is present as a mixture of stereoisomers. In yet another embodiment, the compound is present as an essentially pure stereoisomer, which stereoisomer may, for example, have the chair, pseudo-rac structure.

As utilized herein, the following terms have the meanings indicated below.

The term "alkyl", means a straight-chain, branched-chain or cyclic alkyl radical. Examples of such radicals include, but are not limited to, methyl, ethyl, n-propyl, isopropyl, n-butyl, isobutyl, sec-butyl, tert-butyl, pentyl, iso-amyl, hexyl, 2-ethylhexyl, octyl, cyclopentyl, cyclohexyl and the like. The cyclic alkyl radicals may be substituted with one or more straight-chain and/or branched-chain alkyl radicals (i.e., may be alkylcycloalkyl radicals such as, e.g., methylcyclohexyl etc.). Conversely, the straight-chain and branched-chain alkyl radicals may be substituted with one or more cyclic alkyl radicals (i.e., may be cycloalkylalkyl radicals such as cyclohexylmethyl etc.). Moreover, unless indicated otherwise, the above alkyl radicals may be substituted by one or more groups preferably and independently selected from halogen (e.g., F, Cl, Br), alkoxy (e.g., methoxy, ethoxy, propoxy, butoxy and the like), hydroxy, amino, monoalkylamino (e.g., methylamino, ethylamino, propylamino and the like) and dialkylamino (e.g., dimethylamino, diethylamino, dipropylamino, diisopropylamino, piperidino and the like) and trihydrocarbylsilyl (e.g., trimethylsilyl, triphenylsilyl and the like). Unless otherwise stated, the above definition of the term "alkyl" also applies to groups comprising one or more alkyl radicals.

The term "alkenyl" means "alkyl" as defined above having one or more double and/or triple bonds. Examples of alkenyl radicals include, but are not limited to, ethenyl, propenyl, allyl, butenyl, propargyl, 1,4-butadienyl, isopropenyl, cyclopentenyl, cyclohexenyl, cyclooctenyl, cyclopentadienyl, cyclohexadienyl, cyclooctadienyl and the like.

The term "alkoxy" means an alkyl or alkenyl ether radical wherein the terms "alkyl" and "alkenyl" are as defined above. Examples of suitable alkyl ether radicals include, but are not limited to, methoxy, ethoxy, n-propoxy, isopropoxy, n-butoxy, iso-butoxy, sec-butoxy, tert-butoxy, allyloxy, trifluoromethoxy and the like.

The term "aryl" means an aromatic radical, for example, a phenyl, naphthyl, azulenyl, phenanthryl or anthracenyl radical and the like which optionally contains one or more (e.g., 2 or 3) heteroatoms (preferably selected from N, O and S and combinations thereof) in the ring and/or carries one or more identical or different substituents, for example, alkoxy, aryl, halogen, hydroxy, amino, monoalkylamino, dialkylamino, nitro, trihydrocarbylsilyl, alkyl-CO, alkylsulfonyl, alkyl-OCO etc., these terms being as defined herein. Illustrative, non-limiting examples of aryl radicals are phenyl, naphthyl, fluorenyl, chlorophenyl, dichlorophenyl, fluorophenyl, perfluorophenyl, hydroxyphenyl, anisyl, biphenyl, nitrophenyl, acetylphenyl, aminophenyl, pyridyl, pyridazyl, quinolyl, and the like. When carbon numbers are given herein for aryl radicals, ring heteroatoms are counted as carbon atoms. Unless otherwise stated, the above definition of the term "aryl" also applies to groups which comprise one or more aryl radicals. For example, the term "aryloxy" means an aryl ether radical wherein the term "aryl" is as defined above.

The term "hydrocarbyl" encompasses alkyl, alkenyl, arylalkyl arylalkenyl and alkylaryl groups wherein the terms "alkyl", "alkenyl" and "aryl" are as defined above. Preferred hydrocarbyl groups comprise 1 to 20, more preferred 1 to 10, and most preferred 1 to 6 carbon atoms. Illustrative, non-limiting examples are methyl, ethyl, propyl and phenyl.

The term "halogen" means fluorine, chlorine, bromine and iodine.

Activators and Activation Methods for Catalyst Precursor Compounds

The catalyst precursor compounds of the present invention, described above, are typically activated in various ways to yield, for example, compounds having a vacant coordination site that will coordinate, insert, and polymerize olefin(s). For the purposes of this patent specification and appended claims, the term "activator" is defined to be any compound which can activate any one of the catalyst precursor compounds described above by converting the neutral catalyst compound to a catalytically active catalyst compound, for example, a cation. Non-limiting examples of activators include alumoxanes, aluminum alkyls, ionizing activators, which may be neutral or ionic, and conventional-type cocatalysts.

Aluminoxane and Aluminum Alkyl Activators

In one aspect, alumoxane activators are utilized as an activator in the catalyst composition of the invention. Alumoxanes are generally oligomeric, cyclic or acyclic, compounds containing —Al(R)—O— subunits (generally about 6 to about 40), where R is an alkyl group. Illustrative, non-limiting examples of alumoxanes include MAO, MMAO, ethyl alumoxane and isobutyl alumoxane. Alumoxanes may be produced by the hydrolysis of the respective trialkylaluminum compound. MMAO may be produced by the hydrolysis of trimethylaluminum and a higher trialkylaluminum compound such as triisobutylaluminum. MMAO's are generally more soluble in aliphatic solvents and more stable during storage. There are a variety of methods for preparing alumoxane and modified alumoxanes, non-limiting examples of which are described in U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP-A-0 561 476, EP-B1-0 279 586, EP-A-0 594-218 and EP-B1-0 586 665, and PCT publications WO 94/10180 and WO 99/15534, all of which are herein fully incorporated by reference. Another alumoxane is a MMAO cocatalyst type 3A (commercially available from Akzo Chemicals, Inc. under the trade name Modified Methylalumoxane type 3A, covered under U.S. Pat. No. 5,041,584, fully incorporated herein by reference).

Illustrative, non-limiting examples of aluminum alkyl compounds which may be utilized as activators for the catalyst precursor compounds of the present invention include trimethylaluminum, triethylaluminum, triisobutylaluminum, tri-n-hexylaluminum, tri-n-octylaluminum and the like.

B. Ionizing Activators

It is also within the scope of this invention to use an ionizing or stoichiometric activator, neutral or ionic, such as, e.g.,tri(n-butyl-ammoniumtetrakis(pentafluorophenyl) boron, a trisperfluorophenyl boron metalloid precursor or a trisperfluoronaphthyl boron metalloid precursor, polyhalogenated heteroborane anions (see, e.g., WO 98/43983, fully incorporated herein by reference), boric acid (see, e.g., U.S. Pat. No. 5,942,459, fully incorporated herein by reference) and combinations thereof. It is also within the scope of this invention to use neutral or ionic activators alone or in combination with alumoxane or modified alumoxane activators.

Non-limiting examples of neutral stoichiometric activators include tri-substituted boron, tellurium, aluminum, gallium, indium, and mixtures thereof. The three substituent groups may each independently be selected from alkyl, alkenyl, halogen, substituted alkyl, aryl, arylhalide, alkoxy and halide radicals. Preferably, the three groups are independently selected from halogen, mono- or polycyclic (including halosubstituted) aryl, alkyl, alkoxy and alkenyl radicals and combinations thereof. Preferred are alkyl groups having 1 to 20 carbon atoms, alkenyl groups having 1 to 20 carbon atoms, alkoxy groups having 1 to 20 carbon atoms and aryl groups having 6 to 20 carbon atoms (including substituted aryl groups). More preferably, the three groups are independently selected from alkyl groups having 1 to 4 carbon groups, phenyl and naphthyl groups. Even more preferably, the three groups are halogenated, preferably fluorinated, aryl groups. Most preferably, the neutral stoichiometric activator is trisperfluorophenyl boron or trisperfluoronaphthyl boron. 'Ionic stoichiometric activator compounds may contain an active proton, or some other cation associated with, but not coordinated to, or only loosely coordinated to, the remaining ion of the ionizing compound. Such compounds are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are fully incorporated herein by reference.

In a preferred embodiment, the stoichiometric activators include a cation and an anion component, and may be represented by Formula II:

$$(L—H)_d^{+}(A^{d-}) \qquad \text{Formula II}$$

wherein L is a neutral Lewis base, H is hydrogen, $(L—H)^+$ is a Bronsted acid, $A^{d-}$ is a non-coordinating anion having the charge d−, and d is an integer from 1 to 3.

In Formula II, the cation component, $(L—H)_d^+$ may include Bronsted acids such as protons or protonated Lewis bases or reducible Lewis acids capable of protonating or abstracting a moiety, such as an alkyl or aryl group, from the catalyst precursor compound, resulting in a cationic transition metal species.

The activating cation $(L—H)_d^+$ may be a Bronsted acid, capable of donating a proton to the catalyst precursor resulting in a transition metal cation, including ammonium, oxonium, phosphonium, silylium species, and mixtures thereof, preferably ammonium species derived from methylamine, aniline, dimethylamine, diethylamine, N-methylaniline, diphenylamine, trimethylamine, triethylamine, N,N-dimethylaniline, methyldiphenylamine, pyridine, p-bromo-N,N-dimethylaniline andp-nitro-N,N-dimethylaniline; phosphonium species derived from triethylphosphine, triphenylphosphine, and diphenylphosphine; oxonium species derived from ethers such as dimethyl ether, diethyl ether, tetrahydrofuran and dioxane; sulfonium species derived from thioethers, such as diethyl thioether and tetrahydrothiophene; and mixtures thereof. The activating cation $(L—H)_d^+$ may also be an abstracting moiety such as a silver, carbonium, tropylium, carbenium, ferrocenium species and mixtures thereof, preferably carbonium or ferrocenium species. Most preferably $(L—H)_d^+$ is triphenylcarbonium.

In Formula II, the anion component $A^{d-}$ includes those having the formula $[M^{k+}Q_n]^{d-}$ wherein k is an integer from 1 to 3; n is an integer from 2 to 6; n−k=d; M is an element selected from Group 13 of the Periodic Table of the Elements, preferably boron or aluminum, and Q is independently selected from hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide. Preferably, each Q is a fluorinated hydrocarbyl group having 1 to 20 carbon atoms; more preferably each Q is a fluorinated aryl group, and most preferably each Q is a pentafluoroaryl group. Non-limiting examples of suitable $A^{d-}$ species also include diboron compounds as disclosed in U.S. Pat. No. 5,447,895, fully incorporated herein by reference.

Most preferably, the ionic stoichiometric activator $(L—H)_d^+$ $(A^{d-})$ is N,N-dimethylanilinium tetra (perfluorophenyl)borate or triphenylcarbenium tetra (perfluorophenyl)borate.

In another embodiment, an activation method using ionizing ionic compounds not containing an active proton but capable of producing a catalyst precursor compound cation and its non-coordinating anion are also contemplated, and are described in EP-A-0 426 637, EP-A-0 573 403 and U.S. Pat. No. 5,387,568, which are all herein fully incorporated by reference.

The mole ratio of the metal or metalloid of the activator component to the metals of the supported linked metallocene catalyst complex are in the range of between 0.3:1 to 1000:1, preferably 20:1 to 800:1, and most preferably 50:1 to 500:1. Where the activator is an ionizing activator such as those based on the anion tetrakis(pentafluorophenyl) boron, the mole ratio of the metal or metalloid of the activator component to the metal component of the metallocene catalyst is preferably in the range of between 0.3:1 to 3:1.

Where an unsupported metallocene catalyst system is utilized, the mole ratio of the metal or metalloid of the activator component to the metals of the linked metallocene catalyst complex is in the range of between 0.3:1 to 10,000:1, preferably 100:1 to 5000:1, and most preferably 500:1 to 2000:1.

Supports, Carriers and General Supporting Techniques

In another embodiment, the catalyst composition of the invention includes a support material or carrier, or a supported activator. For example, the catalyst composition of the invention or one or more of the individual components thereof may be deposited on, contacted with, vaporized with, bonded to, incorporated within, adsorbed or absorbed in, or on, a support or carrier.

Support Material

The support material may be any of the conventional support materials. Preferably the support material is a porous support material selected from, for example, talc, inorganic oxides and inorganic chlorides. Other support materials include resinous support materials such as polystyrene, functionalized or crosslinked organic supports, such as polystyrene divinyl benzene polyolefins or polymeric compounds, zeolites, clays, or any other organic or inorganic support material, or mixtures thereof.

The preferred support materials are inorganic oxides, more preferably those selected from oxides of elements of Groups 2, 3, 4, 5, 13 and 14 of the Periodic Table of Elements, and combinations thereof. The more preferred supports include silica, fumed silica, alumina (see, e.g., WO 99/60033, fully incorporated herein by reference), silica-alumina and mixtures thereof. Other useful supports include magnesia, titania, zirconia, magnesium chloride (see, e.g., U.S. Pat. No. 5,965,477, fully incorporated herein by reference), montmorillonite (see, e.g., European Patent EP-B1 0 511 665, fully incorporated herein by reference), phyllosilicate, zeolites, talc, clays (see, e.g., U.S. Pat. No. 6,034,187, fully incorporated herein by reference) and the like. Also, combinations of these support materials may be used, for example, silica-chromium, silica-alumina, silica-titania and the like. Additional non-limiting examples of support materials include the porous acrylic polymers described in EP 0 767 184 B1; nanocomposites as described in PCT WO 99/47598; aerogels as described in WO 99/48605, spherulites as described in U.S. Pat. No. 5,972, 510; and polymeric beads as described in WO 99/50311, which are all herein incorporated by reference. Another preferred support is fumed silica available under the trade name Cabosil™ TS-610, available from Cabot Corporation. Fumed silica is typically a silica with particles 7 to 30 nanometers in size that has been treated with dimethylsilyldichloride such that a majority of the surface hydroxyl groups are capped.

It is preferred that the support material, most preferably an inorganic oxide, has a surface area in the range of from about 10 to about 700 m²/g, a pore volume in the range of from about 0.1 to about 4.0 cc/g and an average particle size in the range of from about 5 to about 500 μm. More preferably, the surface area of the support material is from about 50 to about 500 m²/g, the pore volume is from about 0.5 to about 3.5 cc/g and the average particle size is from about 10 to about 200 μm. Most preferably the surface area of the support material is from about 100 to about 400 m²/g, the pore volume is from about 0.8 to about 3.0 cc/g and the average particle size is from about 5 to about 100 μm. The average pore size of the support typically is from 10 to 1000 Å, preferably about 50 to about 500Å, and most preferably about 75 to about 350 Å.

The support materials may be treated chemically, for example with a fluoride compound as described in WO 00/12565, which is fully incorporated herein by reference. Other supported activators are described in, for example, WO 00/13792 (fully incorporated herein by reference), that refers to supported boron containing solid acid complex.

In a preferred method of forming a supported catalyst composition component, the amount of liquid in which the activator is present is less than about four times the pore volume of the support material, more preferably less than three times, even more preferably less than two times; preferred ranges being from about 1.1 times to about 3.5 times and most preferably about 1.2 to about 3 times. In an alternative embodiment, the amount of liquid in which the activator is present is from one to less than one times the pore volume of the support material utilized in forming the supported activator.

Procedures for measuring the total pore volume of a porous support are well known in the art. Details of one of these procedures are discussed in Volume 1, *Experimental Methods in Catalytic Research* (Academic Press, 1968) (specifically see pages 67–96). This preferred procedure involves the use of a classical BET apparatus for nitrogen absorption. Another method well known in the art is described in Innes, *Total Porosity and Particle Density of Fluid Catalysts By Liquid Titration*, Vol. 28, No. 3, Analytical Chemistry 332–334 (March, 1956). All of these documents are fully incorporated herein by reference.

B. Supported Activators

In another embodiment, the catalyst composition includes a supported activator. Many supported activators are described in various patents and publications which include: U.S. Pat. No. 5,728,855 directed to the forming a supported oligomeric alkylaluminoxane formed by treating a trialkylaluminum with carbon dioxide prior to hydrolysis; U.S. Pat. Nos. 5,831,109 and 5,777,143 discuss a supported methylalumoxane made using a non-hydrolytic process; U.S. Pat. No. 5,731,451 relates to a process for making a supported alumoxane by oxygenation with a trialkylsiloxy moiety; U.S. Pat. No. 5,856,255 discusses forming a supported auxiliary catalyst (alumoxane or organoboron compound) at elevated temperatures and pressures; U.S. Pat. No. 5,739,368 discusses a process of heat treating alumoxane and placing it on a support; EP-A-0 545 152 relates to adding a metallocene to a supported alumoxane and adding more methylalumoxane; U.S. Pat. Nos. 5,756,416 and 6,028,151 discuss a catalyst composition of an alumoxane impregnated support and a metallocene and a bulky aluminum alkyl and methylalumoxane; EP-B1-0 662 979 discusses the use of a metallocene with a catalyst support of silica reacted with alumoxane; PCT WO 96/16092 relates to a heated support treated with alumoxane and washing to remove unfixed alumoxane; U.S. Pat. Nos. 4,912,075, 4,937,301, 5,008,228, 5,086,025, 5,147,949, 4,871,705, 5,229,478, 4,935,397, 4,937,217 and 5,057,475, and PCT WO 94/26793 all are directed to adding a metallocene to a supported activator; U.S. Pat. No. 5,902,766 relates to a supported activator having a specified distribution of alumoxane on the silica particles; U.S. Pat. No. 5,468,702 relates to aging a supported activator and adding a metallocene; U.S. Pat. No. 5,968,864 discusses treating a solid with alumoxane and introducing a metallocene; EP 0 747 430 A1 relates to a process using a metallocene on a supported methylalumoxane and trimethylaluminum; EP 0 969 019 A1 discusses the use of a metallocene and a supported activator; EP-B2-0 170 059 relates to a polymerization process using a metallocene and a organo-aluminuim compound, which is formed by reacting aluminum trialkyl with a water containing support; U.S. Pat. No. 5,212,232 discusses the use of a supported alumoxane and a metallocene for producing styrene based polymers; U.S. Pat. No. 5,026,797 discusses a polymerization process using a solid component of a zirconium compound and a water-insoluble porous inorganic oxide preliminarily treated with alumoxane; U.S. Pat. No. 5,910,463 relates to a process for preparing a catalyst support by combining a dehydrated support material, an alumoxane and a polyfunctional organic crosslinker; U.S. Pat. Nos. 5,332,706, 5,473,028, 5,602,067 and 5,420,220 discuss a process for making a supported activator where the volume of alumoxane solution is less than the pore volume of the support material; WO 98/02246 discusses silica treated with a solution containing a source of aluminum and a metallocene; WO 99/03580 relates to the use of a supported alumoxane and a metallocene; EP-A1-0 953 581 discloses a heterogeneous catalytic system of a supported alumoxane and a metallocene; U.S. Pat. No. 5,015,749 discusses a process for preparing a polyhydrocarbyl-alumoxane using a porous organic or inorganic imbiber material; U.S. Pat. Nos. 5,446,001 and 5,534,474 relate to a process for preparing one or more alkylaluminoxanes immobilized on a solid, particulate inert support; and EP-A1-0 819 706 relates to a process for preparing a solid silica treated with alumoxane. All of the above-mentioned documents are fully incorporated herein by reference. Also, the following articles, also fully incorporated herein by reference for purposes of disclosing useful supported activators and methods for their preparation, may be referred to: W. Kaminsky, et al., "Polymerization of Styrene with Supported Half-Sandwich Complexes", Journal of Polymer Science Vol. 37, 2959–2968 (1999) describes a process of adsorbing a methylalumoxane to a support followed by the adsorption of a metallocene; Junting Xu, et al. "Characterization of isotactic polypropylene prepared with dimethylsilylbis(1-indenyl) zirconium dichloride supported on methylaluminoxane pretreated silica", European Polymer Journal 35 (1999) 1289–1294, discusses the use of silica treated with methylalumoxane and a metallocene; Stephen O'Brien, et al., "EXAFS analysis of a chiral alkene polymerization catalyst incorporated in the mesoporous silicate MCM-41" Chem. Commun. 1905–1906 (1997) discloses an immobilized alumoxane on a modified mesoporous silica; and F.Bonini, et al., "Propylene Polymerization through Supported Metallocene/MAO Catalysts: Kinetic Analysis and Modeling" Journal of Polymer Science, Vol. 33, 2393–2402 (1995) discusses using a methylalumoxane supported silica with a metallocene. Any of the methods discussed in these references are useful for producing the supported activator component utilized in the catalyst composition of the invention and all are incorporated herein by reference.

In another embodiment, the supported activator, such as supported alumoxane, is aged for a period of time prior to use herein. For reference please refer to U.S. Pat. Nos. 5,468,702 and 5,602,217, fully incorporated herein by reference.

In another embodiment, the supported activator is in a dried state or a solid. In another embodiment, the supported activator is in a substantially dry state or a slurry, preferably a mineral oil slurry.

In another embodiment, two or more separately supported activators are used, or alternatively, two or more different activators on a single support are used.

In another embodiment, the support material, preferably partially or totally dehydrated support material, preferably 200° C. to 600° C. dehydrated silica, is contacted with an organoaluminum or alumoxane compound. Preferably, when an organoaluminum compound is used, the activator is formed in situ on and in the support material as a result of the reaction of, for example, trimethylaluminum and water.

In another embodiment, Lewis base-containing supports are reacted with a Lewis acidic activator to form a support bonded Lewis acid compound. The Lewis base hydroxyl groups of silica are exemplary of metal/metalloid oxides where this method of bonding to a support occurs. This embodiment is described in U.S. patent application Ser. No. 09/191,922, filed Nov. 13, 1998, which is fully incorporated herein by reference.

Other examples of supporting an activator are described in U.S. Pat. No. 5,427,991, where supported non-coordinating anions derived from trisperfluorophenyl boron are described; U.S. Pat. No. 5,643,847 discusses the reaction of Group 13 Lewis acid compounds with metal oxides such as silica and illustrates the reaction of trisperfluorophenyl boron with silanol groups (the hydroxyl groups of silica) resulting in bound anions capable of protonating transition metal organometallic catalyst compounds to form catalytically active cations counter-balanced by the bound anions; immobilized Group IIIA Lewis acid catalysts suitable for carbocationic polymerizations are described in U.S. Pat. No. 5,288,677; and James C. W. Chien, Jour. Poly. Sci.: Pt A: Poly. Chem., Vol. 29, 1603–1607 (1991), describes the olefin polymerization utility of methylalumoxane (MAO) reacted with silica ($SiO_2$) and metallocenes and describes a covalent bonding of the aluminum atom to the silica through an oxygen atom of the surface hydroxyl groups of the silica. All of the above documents are fully incorporated herein by reference.

In a preferred embodiment, a supported activator is formed by preparing in an agitated, and temperature and pressure controlled vessel a solution of the activator and a suitable solvent, then adding the support material at temperatures from 0° C. to 100° C., contacting the support with the activator solution for up to 24 hours, then using a combination of heat and pressure to remove the solvent to produce a free flowing powder. Temperatures can range from 40 to 120° C. and pressures from 5 psia to 20 psia (34.5 to 138 kPa). An inert gas sweep can also be used to assist in removing solvent. Alternate orders of addition, such as slurrying the support material in an appropriate solvent then adding the activator, can be used.

Polymerization Process

The catalyst compositions of the present invention and the methods of catalyst composition addition described above are suitable for use in any prepolymerization and/or polymerization process over a wide range of temperatures and pressures. The temperatures may be in the range of from −60° C. to about 280° C., preferably from 50° C. to about 200° C. In one embodiment, the polymerization process is conducted above 70° C. and preferably above 80° C. The pressures employed may be in the range from 1 atmosphere to about 500 atmospheres or higher.

Polymerization processes include solution, gas phase, slurry phase, high pressure processes and combinations thereof Particularly preferred is a gas phase or slurry phase polymerization of one or more olefins at least one of which is ethylene or propylene.

In one embodiment, the process of this invention is directed toward a solution, high pressure, slurry or gas phase polymerization process of one or more olefin monomers having from 2 to 30 carbon atoms, preferably 2 to 12 carbon atoms, and more preferably 2 to 8 carbon atoms. The invention is particularly well suited for the polymerization of two or more olefin monomers selected from ethylene, propylene, butene-1, pentene-1, 4-methyl-pentene-1, hexene-1, octene-1 and decene-1.

Other monomers useful in the process of the invention include ethylenically unsaturated monomers, diolefins having 4 to 18 carbon atoms, conjugated or nonconjugated dienes, polyenes, vinyl monomers and cyclic olefins. Non-limiting examples of such monomers include norbornene, norbornadiene, isobutylene, isoprene, vinylbenzocyclobutane, styrenes, alkyl substituted styrene, ethylidene norbornene, dicyclopentadiene and cyclopentene.

In the most preferred embodiment of the process of the invention, a copolymer of ethylene is produced, where together with ethylene, at least one comonomer having from 3 to 15 carbon atoms, preferably from 4 to 12 carbon atoms, and most preferably from 4 to 8 carbon atoms, is polymerized in a gas phase process.

In another aspect of the process of the invention, ethylene or propylene is polymerized with at least two different comonomers, optionally one of which may be a diene, to form a terpolymer.

In still another aspect, the molar ratio of comonomer to ethylene, $C_x/C_2$, where $C_x$ is the amount of comonomer and $C_2$ is the amount of ethylene is from about 0.001 to about 0.200, and more preferably from about 0.002 to about 0.008.

In another aspect of the process of the invention, propylene is polymerized either alone or with one or more comonomers including ethylene and/or other olefins having 4 to 12 carbon atoms, particularly in a gas phase or slurry phase process.

Typically in a gas phase polymerization process a continuous cycle is employed where in one part of the cycle of a reactor system, a cycle gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228, all of which are fully incorporated herein by reference.)

The reactor pressure in a gas phase process may vary from about 100 psig (690 kPa) to about 600 psig (4138 kPa), preferably from about 200 psig (1379 kPa) to about 400 psig (2759 kPa), more preferably in the range of from about 250 psig (1724 kPa) to about 350 psig (2414 kPa).

The reactor temperature in a gas phase process may vary from about 30° C. to about 120° C., preferably from about 60° C. to about 115° C., more preferably from about 70° C. to about 110° C., and most preferably from about 70° C. to about 95° C.

Other gas phase processes contemplated by the process of the invention include series or multistage polymerization processes. Further gas phase processes contemplated by the invention include those described in U.S. Pat. Nos. 5,627, 242, 5,665,818 and 5,677,375, and European publications EP-A- 0 794 200 EP-B1-0 649 992, EP-A- 0 802 202 and EP-B- 634 421, all of which are herein fully incorporated by reference.

In a preferred embodiment, the reactor utilized in the present invention is capable of and the process of the invention is producing greater than 500 lbs of polymer per hour (227 Kg/hr) to about 200,000 lbs/hr (90,900 Kg/hr) or higher of polymer, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and most preferably greater than 65,000 lbs/hr (29,000 Kg/hr) to greater than 100,000 lbs/hr (45,500 Kg/hr).

A slurry polymerization process generally uses pressures in the range of from about 1 to about 50 atmospheres and even greater and temperatures in the range from about 0° C. to about 120° C. In a slurry polymerization, a suspension of solid, particulate polymer is formed in a liquid polymerization diluent medium to which ethylene and comonomers and often hydrogen along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

A preferred polymerization technique of the invention is referred to as a particle form polymerization, or a slurry process where the temperature is kept below the temperature at which the polymer goes into solution. Such technique is well known in the art, and described in, for instance, U.S. Pat. No. 3,248,179 which is fully incorporated herein by reference. Other slurry processes include those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484 and 5,986,021, which are herein fully incorporated by reference.

In an embodiment the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

Examples of solution processes are described in U.S. Pat. Nos. 4,271,060, 5,001,205, 5,236,998, 5,589,555 and 5,977, 251 and PCT WO 99/32525 and PCT WO 99/40130, all of which are fully incorporated herein by reference.

A preferred process of the invention is where the process, preferably a slurry or gas phase process, is operated in the presence of a catalyst composition of the invention and in the absence of or essentially free of any scavengers, such as triethylaluminum, trimethylaluminum, tri-isobutylaluminum and tri-n-hexylaluminum and diethyl aluminum chloride, dibutyl zinc and the like. This preferred process is described in PCT publication WO 96/08520 and U.S. Pat. No. 5,712,352 and 5,763,543, all of which are herein fully incorporated by reference.

In another aspect of the process of the invention, olefin(s), preferably $C_2$ to $C_{30}$ olefin(s) or alpha-olefin(s), are prepolymerized in the presence of the catalyst composition of the invention described above prior to the main polymerization. The prepolymerization can be carried out batchwise or continuously in gas, solution or slurry phase including at elevated pressures. The prepolymerization can take place with any olefin monomer or combination and/or in the presence of any molecular weight controlling agent such as hydrogen. For examples of prepolymerization procedures, see U.S. Pat. Nos. 4,748,221, 4,789,359, 4,923,833, 4,921, 825, 5,283,278 and 5,705,578 and European publication EP-B-0279 863 and PCT Publication WO 97/44371, all of which are herein fully incorporated by reference.

Polymer Products

The polymers produced by the process of the invention can be used in a wide variety of products and end-use applications. The polymers produced by the process of the invention include linear low density polyethylene, elastomers, plastomers, high density polyethylenes, medium density polyethylenes, low density polyethylenes, polypropylene and polypropylene copolymers.

The polymers, typically ethylene based polymers, have a density in the range of from about 0.86 g/cc to about 0.97 g/cc, preferably in the range of from about 0.88 g/cc to about 0.965 g/cc, more preferably in the range of from about 0.900 g/cc to about 0.96 g/cc, even more preferably in the range of from about 0.905 g/cc to about 0.95 g/cc, yet even more preferably in the range from about 0.910 g/cc to about 0.940 g/cc, and most preferably greater than 0.915 g/cc, preferably greater than 0.920 g/cc, and most preferably greater than 0.925 g/cc. Density is measured in accordance with ASTM-D-1238.

The polymers produced by the process of the invention typically have a molecular weight distribution, weight average molecular weight to number average molecular weight ($M_w/M_n$), as determined by GPC using techniques well known in the art, of from about 1.5 to about 15, particularly about 2 to about 10, more preferably about 2.2 to about 8, and most preferably from about 2.5 to about 8.

The polymers of the present invention in one embodiment have a melt index (MI or $I_2$) as measured according to ASTM-D-1238-E in the range from no measurable flow to about 1000 dg/min, more preferably from about 0.01 dg/min to about 100 dg/min, even more preferably from about 0.1 dg/min to about 50 dg/min, and most preferably from about 0.1 dg/min to about 10 dg/min.

The polymers of the invention in a preferred embodiment have a melt index ratio ($I_{21}/I_2$) ($I_{21}$ is measured according to ASTM-D-1238-F) of from preferably greater than about 25, more preferably greater than 30, even more preferably greater that 40, still even more preferably greater than 50 and most preferably greater than 65.

In yet another aspect, propylene based polymers are produced in the process of the invention. These polymers include atactic polypropylene, isotactic polypropylene, hemi-isotactic and syndiotactic polypropylene. Other propylene polymers include propylene block or impact copolymers. Propylene polymers of these types are well known in the art, see, for example, U.S. Pat. Nos. 4,794,096, 3,248,455, 4,376,851, 5,036,034 and 5,459,117, all of which are fully incorporated herein by reference.

The polymers of the invention may be blended and/or coextruded with any other polymer. Non-limiting examples of other polymers include linear low density polyethylenes, elastomers, plastomers, high pressure low density polyethylene, high density polyethylenes, polypropylenes and the like.

Polymers produced by the process of the invention and blends thereof are useful in such forming operations as film, sheet, and fiber extrusion and co-extrusion as well as blow molding, injection molding and rotary molding. Films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fibers include melt spinning, solution spinning and melt blown fiber operations for use in woven or non-woven form to make filters, diaper fabrics, medical garments, geotextiles, etc. Extruded articles include medical tubing, wire and cable coatings, pipe, geomembranes, and pond liners. Molded articles include single and multi-layered constructions in the form of bottles, tanks, large hollow articles, rigid food containers and toys, etc.

Unless otherwise stated, all percentages, parts, ratios, etc., utilized herein, are by weight.

Also, unless otherwise stated, a reference to a compound or component (e.g., the catalyst precursor compounds of the present invention) includes the compound or component by itself, any of its individual stereoisomers (e.g., rac and meso) and any mixtures thereof, as well as any combination with other compounds or components, such as mixtures of compounds.

Further, when an amount, concentration, or other value or parameter, is given as a list of upper preferable values and lower preferable values, this is to be understood as specifically disclosing all ranges formed from any pair of an upper preferred value and a lower preferred value, regardless whether ranges are separately disclosed. Moreover, the upper and lower values of any two (or more) ranges given for a specific parameter are to be understood as also disclosing the ranges formed by combining the lower value of a first range with the upper value of a second range and vice versa.

The following examples further illustrate the invention.

EXAMPLES

All reactions were performed using standard air-free techniques.

Example 1

Preparation of Trans-2-(1-Indenyl)-cyclohexanol (1)

A solution of 29.4 g of indene (0.25 mol) in 500 mL of dry hexane was reacted with 100 mL of n-butyllithium (2.5M in hexanes, 0.25 mol) at room temperature. After 2 hrs. the slurry was chilled in ice water and a solution of 24.5 g of cyclohexene oxide (0.25 mol) in 200 mL of dry hexane added during 8 hrs. After warming to room temperature the slurry was stirred overnight. The resulting mixture was treated with aqueous ammonium chloride and the resulting organic layer was separated and washed with water and then with brine. After drying over sodium sulfate, the solution was evaporated to yield 47 g of crude title compound. Purification was achieved by chromatographing in two portions using 250 g of silica gel, eluting initially with 9:1 hexane:ethyl acetate and ultimately with 2:1 hexane:ethyl acetate. The total yield of purified trans-2-(1-indenyl)-cyclohexanol was 20.0 g (0.0935 mol, 37% yield based on indene). $^1$H NMR (500 MHz, apparent coupling constant in Hz, CDCl$_3$) δ7.48 (1H, m), 7.46 (1H, m), 7.29 (1H, tm, J=7.6), 7.21 (1H, td, J=7.6, 1.2), 6.34 (1H, t, 0.8), 3.84 (1H, td, J=9.89, 4.4), 3.37 (2H, m), 2.63 (1H, m), 2.14 (1H, m), 1.98 (1H, dm, J=13.4), 1.92 (1H, br s), 1.86 (1H, m), 1.76 (1H, dm, J=12.0), 1.5–1.3 (4H, m).

Example 2

Preparation of cis-1,2-bis(1-Indenyl)cyclohexane (2)

A solution of 5.3 g of trans-2-(1-indenyl)-cyclohexanol (25 mmol) and 2.0 mL of pyridine (25 mmol) in 75 mL of CH$_2$Cl$_2$ was chilled in ice water and treated with 4.0 mL of trifluoromethanesulfonic anhydride (24 mmol). After 15 minutes, the solution was washed with cold water, cold brine and dried by stirring over sodium sulfate at 0° C.

The solution was then decanted and evaporated at 0° C. to a colorless residue, which was kept in an ice bath under argon. To this was slowly added a solution of indenyl lithium, made by reacting 3.3 g of indene (28 mmol) in 50 mL dioxane with 14.9 mL of n-butyllithium (1.6M in hexanes, 24 mmol). After 1 hour, the solution was warmed to room temperature and stirred overnight. The solution was diluted with hexane, washed with water and then brine, and then dried over sodium sulfate. After evaporation, 6 g of crude product was obtained. Chromatography on 300 g silica gel (50:1 hexane:ethyl acetate) yielded 1.5 g of the title compound as a mixture of double bond isomers.

Example 3

Preparation of Dilithium Salt of cis-1,2-bis(1-Indenyl)cyclohexane (3)

A solution of 1.5 g of cis-1,2-bis(1-indenyl)cyclohexane (4.8 mmol) in 50 mL hexane was treated with 3.8 mL of n-butyllithium (2.5M in hexanes, 9.6 mmol). The resulting light yellow suspension was stirred for 20 hours before filtering and washing the solids with hexane. After vacuum drying, 1.48 g of white solids were obtained (95% yield). ). $^1$H NMR (300 MHz, apparent coupling constant in Hz, THF-d8): δ7.30 (2H, d, J=7.7), 6.96 (2H, dm, J=7.7), 6.61 (2H, d, J=3.4), 6.23 (2H, tm, J=7.2), 6.14 (2H, tm, J=7.3), 5.62 (2H, d, J=3.3), 4.00 (2H, m), 2.36 (2H, m), 1.98 (2H, m), 1.88 (2H, m), 148 (2H, m).

Example 4

Preparation of Rac-like Isomer of cis-1,2-Cyclohexylenebis (1-indenyl)zirconium Dichloride (4a)

A slurry of 1.33 g of dilithium salt of cis-1,2-bis(1-indenyl)cyclohexane (4.10 mmol) and 1.55 g of ZrCl$_4$(THF)$_2$ (4.10 mmol) in 30 mL of toluene was stirred for four days. After filtering and washing the solids with toluene, the filtrate was evaporated to afford 1.54 g of orange solids which were triturated with toluene to yield 50 mg of pure title compound. $^1$H NMR (500 MHz, apparent coupling constant in Hz, THF-d8): δ7.79 (1H, dq, J=8.9, 0.9), 7.70

(1H, dq, J=8.8, 0.9), 7.39 (1H, dt, J=8.8, 1.1), 7.34 (1H, dt, J=8.1, 1.1), 7.19 (2H, m), 7.14-7.00 (5H, m), 6.72 (1H, d, J=3.4), 6.65 (dd, J=3.4, 0.9), 6.59 (1H, d, J=3.6), 6.53 (1H, dd, 3.6, 1.0), 4.60 (ddd, J=6.7, 5.6, 2.8), 4.01 (ddd, J=12.7, 6.6, 5.5), 2.73 (1H, dq, J=13.1, 4), 2.61 (qd, J=13.1, 3.9), 2.17 (1H, dm, J=13.3 2.10 (1H, m), 1.82 (1H, dm, J=13.6), 1.78 (dt, J=13.1, 3.3), 1.69 (1H, dt, J=13.3, 3.9), 1.58 (1H, qt, J=13.1, 3.8).

Structure as determined by x-ray crystallography:

$[C_6H_{10}(C_9H_6)_2]ZrCl_2$ in P2(1)/n a=9.819 A, b=16.841 A, c=14.320 A, alpha 90, beta=102.24, gamma=90

| | | | |
|---|---|---|---|
| Zr 4 | 0.00000 | 0.00000 | 0.00000 |
| Cl1 3 | 1.85007 | −1.04158 | 1.17806 |
| Cl2 3 | −1.62300 | −1.75124 | 0.33919 |
| C1 1 | −1.02124 | 2.26811 | 0.15673 |
| C2 1 | 0.26555 | 2.36444 | 0.71880 |
| H2A 2 | 0.95844 | 2.86263 | 0.34919 |
| C3 1 | 0.37456 | 1.65183 | 1.85217 |
| H3A 2 | 1.14770 | 1.52557 | 2.35349 |
| C4 1 | −0.90830 | 1.12936 | 2.13937 |
| C5 1 | −1.34671 | 0.25672 | 3.21886 |
| H5A 2 | −0.75257 | −0.07630 | 3.85213 |
| C6 1 | −2.64798 | −0.03975 | 3.25014 |
| H6A 2 | −2.95967 | −0.54640 | 3.96488 |
| C7 1 | −3.57349 | 0.35955 | 2.28245 |
| H7A 2 | −4.46480 | 0.10656 | 2.36420 |
| C8 1 | −3.17835 | 1.11966 | 1.21569 |
| H8A 2 | −3.79623 | 1.37325 | 0.56848 |
| C9 1 | −1.79490 | 1.52741 | 1.09849 |
| C10 1 | −1.43601 | 2.93168 | −1.10683 |
| H10A 2 | −1.40439 | 3.89544 | −0.93198 |
| C11 1 | −2.86127 | 2.63632 | −1.63521 |
| H11A 2 | −2.98951 | 1.67573 | −1.67599 |
| H11B 2 | −3.50997 | 2.99520 | −1.00978 |
| C12 1 | −3.12279 | 3.23105 | −3.01717 |
| H12A 2 | −4.01127 | 2.97205 | −3.30790 |
| H12B 2 | −3.10344 | 4.19856 | −2.95207 |
| C13 1 | −2.13974 | 2.79881 | −4.03542 |
| H13A 2 | −2.33417 | 3.23716 | −4.87870 |
| H13B 2 | −2.21439 | 1.84123 | −4.17043 |
| C14 1 | −0.74466 | 3.13482 | −3.60928 |
| H14A 2 | −0.63012 | 4.09701 | −3.65374 |
| H14B 2 | −0.12365 | 2.73620 | −4.23876 |
| C15 1 | −0.37755 | 2.65807 | −2.18214 |
| H15A 2 | 0.40408 | 3.18862 | −1.92163 |
| C16 1 | 0.09920 | 1.18534 | −2.17026 |
| C17 1 | −0.63338 | 0.01846 | −2.38763 |
| H17A 2 | −1.54041 | −0.01418 | −2.59013 |
| C18 1 | 0.21865 | −1.11642 | −2.25263 |
| H18A 2 | −0.04682 | −2.00602 | −2.30548 |
| C19 1 | 1.55161 | −0.65237 | −2.02170 |
| C20 1 | 2.83426 | −1.29025 | −1.94076 |
| H20A 2 | 2.93482 | −2.20690 | −2.06156 |
| C21 1 | 3.90416 | −0.47348 | −1.67556 |
| H21A 2 | 4.73655 | −0.87526 | −1.57231 |
| C22 1 | 3.83859 | 0.89965 | −1.55055 |
| H22A 2 | 4.60554 | 1.39200 | −1.36544 |
| C23 1 | 2.61606 | 1.53715 | −1.70437 |
| H23A 2 | 2.55387 | 2.46121 | −1.62036 |
| C24 1 | 1.44431 | 0.75254 | −1.99555 |

Example 5

Preparation of Meso-like Isomer of cis-1,2-Cyclohexylenebis(1-indenyl)-zirconium Dichloride (5a)

A solution of 643 mg of tetrakis(dimethylamido) zirconium (2.4 mmol) in 2 mL hexane was combined with a solution of 0.74 g of cis-1,2-bis(1-indenyl)-cyclohexane (2.4 mmol) in 10 mL of hexane. The mixture was stirred under a very slow purge of argon for 3 days before adding 1.21 mL of trimethylsilyl chloride (9.6 mmol) and subsequently stirring for 6 days. The resultant yellow slurry was filtered and the filtrate evaporated to give 0.855 g of yellow powder. Recrystallization gave a quantitity of x-ray quality crystals. $^1$H NMR (300 MHz, apparent coupling constant in Hz, THF-d8): δ7.63 (2H, dq, J=8.6, 1.0), 7.36 (2H, dt, J=8.5, 1.1), 7.05 (2H, ddd, J=8.6, 6.6, 0.8), 6.95 (2H, ddd, J=8.7, 6.6, 0.9), 6.81 (2H, d, J=3.6), 6.58 (2H, dd, J=3.4, 0.7), 4.43 (2H, m), 2.18 (4H, m), 1.96 (2H, m), 1.68 (2H, m).

Structure as determined by x-ray crystallography:

Orthogonal Angstrom coordinates for meso-like $C_{24}H_{22}ZrCl_2$ in P2(1)/n unit cell: a=9.6247, b=19.3320, c=12.7786, alpha=90, beta=103.6959, gamma=90

| | | | |
|---|---|---|---|
| Zr 4 | 0.00000 | 0.00000 | 0.00000 |
| Cl1 3 | −2.10092 | −1.12763 | −0.34059 |
| Cl2 3 | −0.59249 | 1.36832 | 1.92033 |
| C1 1 | 2.31488 | −0.85969 | 0.15132 |
| C2 1 | 1.88959 | −0.63158 | 1.46299 |
| H2A 2 | 2.24400 | 0.01257 | 2.03254 |
| C3 1 | 0.84862 | −1.51640 | 1.79777 |
| H3A 2 | 0.35787 | −1.51253 | 2.58766 |
| C4 1 | 0.68189 | −2.41650 | 0.71246 |
| C5 1 | −0.14457 | −3.54085 | 0.52890 |
| H5A 2 | −0.74014 | −3.80705 | 1.19176 |
| C6 1 | −0.05171 | −4.22849 | −0.64001 |
| H6A 2 | −0.59370 | −4.97219 | −0.77382 |
| C7 1 | 0.83889 | −3.84358 | −1.64469 |
| H7A 2 | 0.87611 | −4.34313 | −2.42830 |
| C8 1 | 1.65132 | −2.76525 | −1.51458 |
| H8A 2 | 2.24923 | −2.54041 | −2.19053 |
| C9 1 | 1.57493 | −1.98617 | −0.33217 |
| C10 1 | 3.39541 | −0.08545 | −0.59897 |
| H10A 2 | 4.11628 | −0.71567 | −0.80716 |
| C11 1 | 3.99332 | 1.02672 | 0.22686 |
| H11A 2 | 4.43179 | 0.64395 | 1.00275 |
| H11B 2 | 3.28086 | 1.60398 | 0.54328 |
| C12 1 | 5.00259 | 1.86399 | −0.55232 |
| H12A 2 | 5.33858 | 2.57812 | 0.01163 |
| H12B 2 | 5.75283 | 1.30859 | −0.81597 |
| C13 1 | 4.34857 | 2.45188 | −1.78132 |
| H13A 2 | 5.00446 | 2.95914 | −2.28471 |
| H13B 2 | 3.64172 | 3.05910 | −1.51176 |
| C14 1 | 3.76805 | 1.36020 | −2.66391 |
| H14A 2 | 4.49809 | 0.84056 | −3.03510 |
| H14B 2 | 3.29853 | 1.77642 | −3.40373 |
| C15 1 | 2.81171 | 0.41564 | −1.94990 |
| H15A 2 | 2.71894 | −0.37350 | −2.52356 |
| C16 1 | 1.43036 | 0.98246 | −1.77533 |
| C17 1 | 0.96766 | 2.04804 | −0.96570 |
| H17A 2 | 1.50030 | 2.55434 | −0.39577 |
| C18 1 | −0.40771 | 2.22821 | −1.14823 |
| H18A 2 | −0.93708 | 2.84703 | −0.69919 |
| C19 1 | −0.85479 | 1.32618 | −2.11497 |
| C20 1 | −2.12729 | 1.10908 | −2.72128 |
| H20A 2 | −2.87053 | 1.60534 | −2.46407 |
| C21 1 | −2.22230 | 0.16239 | −3.67903 |
| H21A 2 | −3.04848 | 0.01353 | −4.07914 |
| C22 1 | −1.13336 | −0.59909 | −4.09145 |
| H22A 2 | −1.25034 | −1.22198 | −4.77204 |
| C23 1 | 0.10315 | −0.45894 | −3.52621 |
| H23A 2 | 0.81776 | −0.99057 | −3.79331 |
| C24 1 | 0.25800 | 0.52873 | −2.51544 |

Toluene molecule of solvation, located on a center of inversion

| | | | |
|---|---|---|---|
| C25 1 | 2.59168 | −1.89956 | −6.13826 |
| C26 1 | 3.60300 | −1.61113 | −5.28056 |
| H26A 2 | 3.76141 | −0.71258 | −5.10066 |
| C27 1 | 4.39766 | −2.50716 | −4.66651 |

-continued

| | | | |
|---|---|---|---|
| H27A 2 | 5.24301 | −2.24831 | −4.37804 |
| C28 1 | 3.97939 | −3.79429 | −4.46040 |
| H28A 2 | 4.37344 | −4.38373 | −3.85860 |
| C29 1 | 2.90382 | −4.10380 | −5.25579 |
| H29A 2 | 2.63525 | −4.99404 | −5.27927 |
| C30 1 | 2.18032 | −3.20099 | −6.03005 |
| H30A 2 | 1.41427 | −3.48304 | −6.47562 |
| C31 1 | 1.81057 | −0.85331 | −6.88403 |
| H31A 2 | 2.09812 | −0.83147 | −7.79972 |
| H31B 2 | 1.95991 | 0.00522 | −6.48109 |
| H31C 2 | 0.87508 | −1.06558 | −6.84741 |

Example 6

Preparation of Meso-like Isomer of cis-1,2-cyclohexylenebis(1-idenyl)zirconium Dimethyl (5b)

A mixture of the rac-like and meso-like isomers of cis-1,2-cyclohexylenebis(1-indenyl)zirconium dichloride (0.528 g, 1.1 mmol), from which the rac-like isomer had been largely removed by crystallization, was dissolved in 15 mL of tetrahydrofuran and treated with 1.7 mL of methyllithium (1.4M in ether, 2.42 mmol) at −78° C. After stirring for 30 minutes, the solution was warmed to room temperature and stirred overnight before concentrating to a dark residue which was extracted with 10 mL of hexane and then filtered to yield 0.189 g of yellow-orange residue. $^1$H NMR (500 MHz, apparent coupling constant in Hz, $C_6D_6$): δ7.34 (2H, dd, J=8.6, 0.8), 7.05 (2H, d, J=7.5), 6.85 (2H, tm, J=8.6), 6.46 (2H, d, J=3.1), 5.88 (2H, d, J=3.5), 3.52 (2H, m), 1.66 (2H, m), 1.59 (4H, m), 1.30 (2H, m), 0.16 (3H, s), −2.19 (3H, s).

The reactions described in Examples 1 to 6 are illustrated in the following Reaction Scheme.

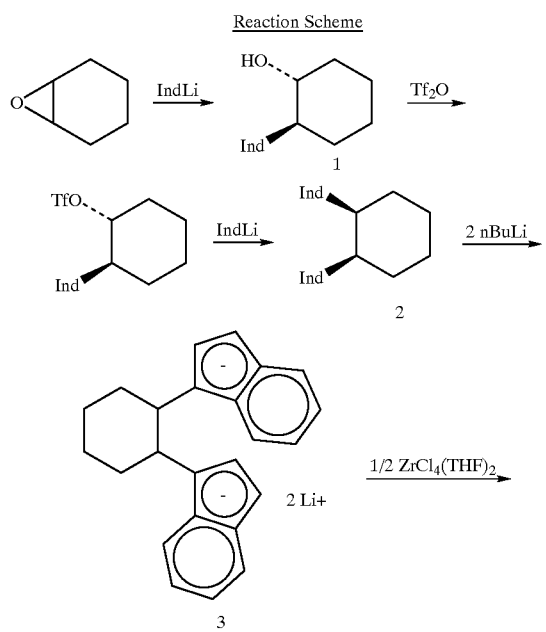

Reaction Scheme

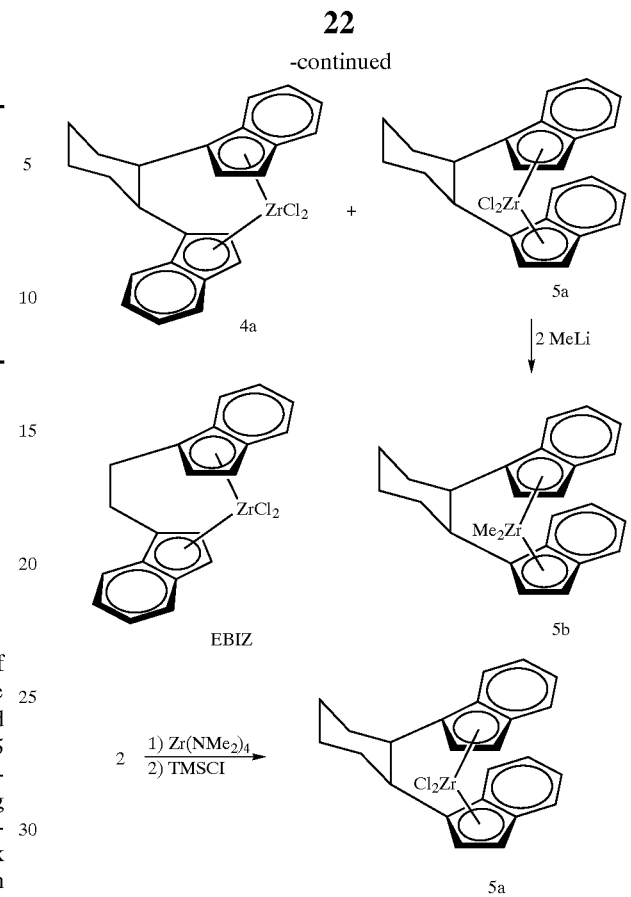

General Procedure for Polymerization

The gases, toluene and hexane were passed through individual sets of one gallon cylinders containing 13× molecular sieves and deoxygenating catalyst before use. The hexane was stored in a 10 gallon tank pressurized under 120 psi of nitrogen while slowly allowing to purge. All reactions were conducted under an atmosphere of purified nitrogen unless stated otherwise.

MMAO (modified methyl alumoxane) type 3A, 1.84M in heptane, was obtained from Akzo. MAO (4.5M in toluene) was obtained from Albemarle. SMAO was prepared as follows: For a 1 kg batch, 1158.43 g of 30 wt % MAO in toluene (7.3 wt % Al, available from Albemarle Corporation, Baton Rouge, La.) and 2,400 g of extra toluene are charged into an 8 liter mix tank equipped with a ribbon helical agitator. 984 g of Davison 955-600 silica is added to the MAO in toluene solution at ambient temperature. A 10° C. exotherm occurs from reaction of the MAO with the hydroxyl groups of the silica. The slurry mixes for 30 minutes at ambient temperature. Drying then occurs by heating the mix tank jacket to about 70° C. and reducing pressure to 0.00 mm Hg. As the slurry thickens the agitator speed is reduced to minimum rotation, about 40–60 RPM. Then the agitator speed is slowly increased (to about 600 RPM) and the temperature is raised to 95° C. as the slurry turns into a dry powder. A nitrogen sweep (about 0.5 cc/min per gram of silica charged) can be used during the end of the drying step to help remove toluene from the silica pores. The material is typically held at 95° C. until toluene removal stops, and material temperature lines out near jacket temperature. The material temperature does not change for at least 30 minutes before the supported methyl alumoxane (SMAO) is considered dry. Residual toluene is reduced to less than 2 wt % on the solids.

A computer controlled, one liter 316 stainless steel reactor with air-operated two-wing paddle and an inner steam-heated shell and an outer water-cooled shell was dried by heating to 135° C. while purging with 500 sccm of nitrogen for 30 minutes. After cooling to 50° C., it was charged with 600 mL of hexane and 43 mL of 1-hexene under inert conditions. A catalyst charging vessel comprising a ¼ inch (0.64 cm)×2" (5 cm) stainless steel tube isolated between two ball valves with a 25 ml stainless steel reservoir on top was charged with the polymerization catalyst in a dry box and then attached to the reactor against a nitrogen purge. The reservoir above the injection tube was pressurized to 250 psi with nitrogen. A solution of 100 micromoles of tri-isobutylaluminum (TIBA) was then added to the reactor and the reactor sealed. When the reactor reached conditions (130 psi ethylene, 85° C., 40 minutes), the catalyst was injected using the nitrogen pressure from the reservoir and held at conditions for the requisite time. The reaction was ended by venting and cooling.

Polymerization Example 8

A mixture of 0.4706 g of SMAO, 10.2 mg of rac-like isomer of cis-1,2-cyclohexylenebis(1-indenyl)zirconium dichloride (4a) and 3.2 ml kaydol oil was stirred for 24 hours. A 0.12 ml aliquot of the deep wine colored mixture was injected into the reactor as described. Polymerization details and results are summarized in the Table below.

Polymerization Example 9

Polymerization Example 8 was repeated, except that before testing the mixture was aged for 96 hours. Polymerization details and results are summarized in the Table below.

Polymerization Example 10 (Comparative)

Polymerization Example 8 was repeated, except that the rac-isomer of ethylenebis(1-indenyl)zirconium dichloride (EBIZ) was used as the zirconium compound.

Polymerization details and results are summarized in Table I below.

TABLE I

| Polymerization Example | Catalyst | Co-catalyst | µmol Zr | Al/Zr | g PE/mmol Zr/100 psi/hr | MI | FI/MI | C4 branch/1000C | Mw | Mw/Mn |
|---|---|---|---|---|---|---|---|---|---|---|
| 1 | CHBIZ | MMAO | 0.2 | 500 | 415040 | 0.07 | 66.5 | 23 | 143230 | 2.82 |
| 2 | CHBIZ | MMAO | 0.2 | 500 | 405281 | 0.05 | 61.4 | 27 | 167000 | 2.23 |
| 3* | EBIZ | MMAO | 0.2 | 500 | 611940 | 1.37 | 38.9 | 17 | 77800 | 2.00 |
| 4* | EBIZ | MMAO | 0.1 | 500 | 492537 | 6.67 | 16.0 | 10 | 66500 | 1.86 |
| 5 | CHBIZ | SMAO | 0.7 | 100 | 138429 | 0.63 | 22.3 | 38 | 119593 | 3.35 |
| 6 | CHBIZ | SMAO | 0.5 | 100 | 157061 | 0.42 | 23.9 | 30 | 127336 | 3.35 |
| 7 | CHBIZ | SMAO | 0.5 | 100 | 171986 | 0.58 | 20.9 | 28 | 128460 | 2.68 |
| 8 | CHBIZ | SMAO | 0.7 | 100 | 118419 | 0.56 | 21.9 | 33 | 117053 | 2.66 |
| 9 | CHBIZ | SMAO | 0.7 | 100 | 127112 | 0.56 | 19.1 | 29 | 118768 | 2.67 |
| 10* | EBIZ | SMAO | 0.35 | 100 | 239134 | 10.94 | 17.4 | 17 | 82285 | 3.59 |

CHBIZ = rac-like isomer of cis-1,2-cyclohexylenebis(1-indenyl)zirconium dichloride (4a)
EBIZ = rac-isomer of ethylenebis(1-indenyl)zirconium dichloride
*comparative

Polymerization Examples 1 and 2

A 0.48 mL aliquot from a stock solution of 10.2 mg of rac-like isomer of cis-1,2-cyclohexylenebis(1-indenyl) zirconium dichloride (4a) (0.021 mmol) in 5 ml of toluene was mixed with 0.11 ml of 1-hexene and then treated with 0.55 ml of MMAO, which produced an amber-colored solution. A 0.11 ml aliquot was injected into the reactor as described. Polymerization details and results are summarized in the Table below.

Polymerization Examples 3 and 4 (Comparative)

Polymerization Examples 1 and 2 were repeated, except that the rac isomer of ethylenebis(1-indenyl)zirconium dichloride (EBIZ) was used as the zirconium compound. Polymerization details and results are summarized in the Table below.

Polymerization Examples 5 to 7

A 1.0 mL aliquot from a stock solution of 10.8 mg of rac-like isomer of cis-1,2-cyclohexylenebis(1-indenyl) zirconium dichloride (4a) (0.023 mmol) in 5 ml toluene was mixed with 0.1025 g of SMAO for 10 minutes. While stirring vigorously, a 0.18 ml aliquot was injected into the reactor as described. Polymerization details and results are summarized in the Table below.

In the above Table, the melt index, MI, is determined according to ASTM-D-1238-E at 190° C. and the flow index, FI, is determined according to ASTM-D-1238-F at 190° C. The branching index, C4 branch/1000 C, which indicates the degree of comonomer (1-hexene) incorporation is determined from IR measurements as described in U.S. Pat. No. 5,527,752, fully incorporated herein by reference. $M_w$ is determined by gel permeation chromatography (GPC) using polystyrene standards. Mw/Mn is determined by size exclusion chromatography.

As is seen from the above results, in comparison to the compound of the present invention, the analogous unconstrained compound with an ethylene bridge instead of a cis-1,2-cyclohexylene bridge (EBIZ) affords much lower molecular weight, much lower comonomer incorporation (as evidenced by the number of butyl branches per 1000 carbon atoms) and a much smaller FI/MI at a comparable molecular weight distribution ($M_w/M_n$) (indicative of long-chain branching).

While the present invention has been described and illustrated by reference to particular embodiments, it will be appreciated by those of ordinary skill in the art, that the invention lends itself to many different variations not illustrated herein. For these reasons, then, reference should be made solely to the appended claims for purposes of determining the true scope of the present invention.

We claimed:

1. A catalyst composition comprising a catalyst precursor compound comprising a metal selected from Groups 4, 5 and 6 of the Periodic Table of Elements and two π-bonded aromatic ring systems linked by a bridging group, wherein the bridging group comprises a ring having 5 to 12 ring members, and wherein the aromatic ring systems are bonded to adjacent members of the ring having 5 to 12 ring members in cis fashion.

2. The catalyst composition of claim 1, wherein the aromatic ring systems are independently selected from cyclopentadienyl and cyclopentadienyl-based systems.

3. The catalyst composition of claim 1, wherein the aromatic ring systems are independently selected from cyclopentadienyl, indenyl, fluorenyl and benzindenyl.

4. The catalyst composition of claim 1, wherein the ring members are independently selected from the group consisting of from B, C, Si, N, P, O, S and combinations thereof.

5. The catalyst composition of claim 4, wherein not more than one of the ring members is different from a carbon atom.

6. The catalyst composition of claim 5, wherein the ring is a cycloaliphatic ring.

7. The catalyst composition of claim 6, wherein the aromatic ring systems are linked by a cis-1,2-cyclohexylene group.

8. A catalyst composition for the polymerization of olefin(s) comprising a catalyst precursor compound represented by the formula

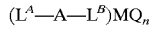

$$(L^A\text{---}A\text{---}L^B)MQ_n$$

wherein

M is a metal selected from Groups 4, 5 and 6 of the Periodic Table of Elements;

$L^A$ and $L^B$ are bonded to M and are independently selected from cyclopentadienyl ligands and cyclopentadienyl-based ligands;

A is a linking group comprising a 5 to 12 membered ring wherein $L^A$ and $L^B$ are bonded to adjacent members of the 5 to 12 membered ring in cis fashion;

each Q is bonded to M and is independently a monoanionic ligand; and n is 0, 1 or 2.

9. The catalyst composition of claim 8, wherein $L^A$ and $L^B$ are independently selected from cyclopentadienyl, 1-indenyl and 9-fluorenyl groups.

10. The catalyst composition of claim 8, wherein $L^A$ and $L^B$ are both indenyl groups.

11. The catalyst composition of claim 8, wherein A comprises a cycloaliphatic ring.

12. The catalyst composition of claim 11, wherein the cycloaliphatic ring is a cyclopentane or cyclohexane ring.

13. The catalyst composition of claim 8, herein M is selected from zirconium and hafnium; $L^A$ and $L^B$ are independently selected from cyclopentadienyl, 1-indenyl and 9-fluorenyl groups; A represents a 6 to 8 membered cycloaliphatic group; the radicals Q are identical and are selected from halogen, $C_1$–$C_6$ alkyl groups, $C_6$–$C_{10}$ aryl groups, $C_7$–$C_{12}$ arylalkyl groups and $C_7$–$C_{12}$ alkylaryl groups; and n is 2.

14. The catalyst composition of claim 8, wherein M is zirconium; $L^A$ and $L^B$ both represent 1-indenyl groups; A represents an unsubstituted cis-1,2-cyclohexylene group; the radicals Q represent chlorine or methyl; and n is 2.

15. The catalyst composition of claim 8 present as a mixture of stereoisomers.

16. The catalyst composition of claim 8 present as an essentially pure stereoisomer.

17. The catalyst composition of claim 16 wherein said stereoisomer has the chair, pseudo-rac structure.

18. The catalyst composition of claim 8 further comprising an activator.

19. The catalyst composition of claim 18, wherein the activator comprises an alumoxane.

20. The catalyst composition of claim 19 further comprising a support.

21. A process for polymerizing of olefin(s) comprising contacting under polymerization conditions, one or more olefin monomers with a catalyst composition comprising a catalyst precursor compound and an activator, the catalyst precursor compound comprising a metal selected from Groups 4, 5 and 6 of the Periodic Table of Elements and two π-bonded aromatic ring systems linked by a bridging group, wherein the bridging group comprises a 5- to 12-membered ring and said aromatic ring systems are bonded to adjacent ring members of said ring in cis fashion.

22. The process of claim 21, wherein the at least one olefin monomers comprise at least one olefin having 2 to 12 carbon atoms.

23. The process of claim 22, wherein the at least one olefin monomers is selected from ethylene, propylene, 1-butene, 1-pentene, 4-methyl-1-pentene, 1-hexene, 1-octene and 1-decene.

24. The process of claim 21, wherein said one or more olefin monomers comprise ethylene and at least one α-olefin having 3 to 8 carbon atoms.

25. A polymer produced by the process of claim 21.

26. The process of claim 22 wherein the catalyst precursor compound is represented by the formula

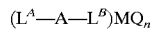

$$(L^A\text{---}A\text{---}L^B)MQ_n$$

wherein

M is an atom selected from Groups 4, 5 and 6 of the Periodic Table of Elements;

$L^A$ and $L^B$ are bonded to Nare independently selected from cyclopentadienyl ligands and cyclopentadienyl-based ligands;

A is a linking group comprising a 5 to 12 membered ring wherein $L^A$ and $L^B$ are bonded to adjacent members of the 5 to 12 membered ring in cis fashion;

each Q is bonded to M and is independently a monoanionic ligand; and n is 0, 1 or2.

27. The process of claim 26, wherein M is selected from zirconium and hafnium; $L^A$ and $L^B$ are independently selected from cyclopentadienyl, 1-indenyl and 9-fluorenyl groups; A represents a 6 to 8 membered cycloaliphatic group; the radicals Q are identical and are selected from halogen, $C_1$–$C_6$ alkyl groups, $C_6$–$C_{10}$ aryl groups, $C_7$–$C_{12}$ arylalkyl groups and $C_7$–$C_{12}$ alkylaryl groups; and n is 2.

28. The process of claim 26, wherein M is zirconium; $L^A$ and $L^B$ both represent 1-indenyl groups; A represents an unsubstituted cis-1,2-cyclohexylene group; the radicals Q represent chlorine or methyl; and n is 2.

* * * * *